(12) United States Patent
Oya et al.

(10) Patent No.: US 8,012,324 B2
(45) Date of Patent: Sep. 6, 2011

(54) SENSOR ELEMENT, METHOD OF MANUFACTURING A SENSOR ELEMENT, AND GAS SENSOR

(75) Inventors: Seiji Oya, Nagoya (JP); Tomohiro Wakazono, Nagoya (JP); Mineji Nasu, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 383 days.

(21) Appl. No.: 11/946,202

(22) Filed: Nov. 28, 2007

(65) Prior Publication Data
US 2008/0121020 A1 May 29, 2008

(30) Foreign Application Priority Data
Nov. 29, 2006 (JP) ................. P2006-322248

(51) Int. Cl.
*G01N 27/407* (2006.01)
*B32B 18/00* (2006.01)
(52) U.S. Cl. ........ 204/426; 204/424; 156/60; 205/783.5
(58) Field of Classification Search .......... 204/424–429; 205/781, 783.5–785; 73/23.31, 23.32, 31.05; 156/60, 89.11–89.28
See application file for complete search history.

(56) References Cited

U.S. PATENT DOCUMENTS

| 4,909,922 | A | * | 3/1990 | Kato et al. | 204/406 |
| 5,676,811 | A | * | 10/1997 | Makino et al. | 204/425 |
| 2001/0047939 | A1 | * | 12/2001 | Springhorn | 204/431 |
| 2003/0034245 | A1 | * | 2/2003 | Diehl | 204/424 |
| 2006/0211123 | A1 | * | 9/2006 | Ker et al. | 436/113 |
| 2006/0220159 | A1 | * | 10/2006 | Matsuo et al. | 257/414 |

FOREIGN PATENT DOCUMENTS

| JP | 61134655 A | * | 6/1986 |
| JP | 9-105737 A | | 4/1997 |
| JP | 2001242129 A | | 9/2001 |
| JP | 2006-300923 A | | 11/2006 |

OTHER PUBLICATIONS

Human translation of JP61134655, 1986.*

* cited by examiner

*Primary Examiner* — Kaj K Olsen
*Assistant Examiner* — Susan Thai
(74) *Attorney, Agent, or Firm* — Sughrue Mion, PLLC

(57) ABSTRACT

A sensor element including: a first solid electrolyte layer as defined herein; and a second solid electrolyte layer as defined herein, wherein the first solid electrolyte layer includes a first inner insulating layer, a first outer insulating layer, a first inner conductive layer and a first outer conductive layer as defined herein, the second solid electrolyte layer includes a second inner insulating layer, a second outer insulating layer, a second inner conductive layer and a second outer conductive layer as defined herein, and the first outer conductive layer and the second outer conductive layer are in contact with one another.

11 Claims, 9 Drawing Sheets

SENSOR ELEMENT, METHOD OF MANUFACTURING A SENSOR ELEMENT, AND GAS SENSOR

BACKGROUND OF THE INVENTION

1. Field of the Invention

The present invention relates to a sensor element having a plurality of solid electrolytes each formed in the shape of a plate extending in a longitudinal direction, through holes penetrating the solid electrolytes in the thicknesswise direction, conductive layers respectively disposed in the through holes so as to form conduction paths, and insulating layers for electrically insulating each of the solid electrolytes and conductive layers. The present invention also relates to a method of manufacturing such a sensor element and to a gas sensor having such a sensor element.

2. Description of the Related Art

Conventionally, sensor elements are known which are formed by stacking a plurality of plate-shaped members (such as solid electrolyte substrates and insulating members) each formed in the shape of a plate extending in a longitudinal direction (JP-A-2001-242129 (FIG. 3 and the like)).

In such a sensor element, in order to electrically connect a first electrode portion disposed on the obverse surface side of the plate-shaped member and a second electrode portion disposed on the reverse surface side of the plate-shaped member, there are cases where a configuration is adopted in which the first electrode member and the second electrode member are electrically connected through a conductive layer disposed in a through hole penetrating the plate-shaped member in the thicknesswise direction.

In addition, the through hole is not limited to a through hole which penetrates a single plate-shaped member, and there are cases where a plurality of connected through holes penetrate a plurality of plate-shaped members. In the sensor element having such connected through holes, the conductive layers disposed in the interior of respective through holes form energizing paths penetrating the plurality of plate-shaped members in the thicknesswise direction (JP-A-9-105737 (FIG. 17 and the like)).

For example, as shown in FIG. 17 of the JP-A-9-105737, leads 12b and 13b of electrodes 12 and 13 of an oxygen sensor portion 3 are connected to terminals 78 by means of through holes 54 of a spacer 5 and through holes 77 of a substrate 80. Namely, through holes 54 and 77 are formed so as to penetrate the plurality of plate-shaped members (the spacer 5 and the substrate 80), and the conductive members disposed in the interiors of these through holes form energizing paths.

3. Problems to be Solved by the Invention

However, since the total thicknesswise dimension of the plate-shaped members is large, the depthwise dimension (lengthwise dimension) of the through hole which penetrates the plurality of plate-shaped members becomes large. Therefore, in cases where the internal conductive layers cannot be appropriately disposed, the energizing path constituted by a conductive layer is possibly broken (disconnected state).

In other words, in the through hole whose lengthwise dimension is large, the operation of inserting the conductive layer into its interior becomes difficult. Consequently, there are cases where the conductive layer becomes disconnected midway in the through hole at the time of inserting the conductive layer, resulting in a faulty energizing path (disconnected state).

Accordingly, the present invention has been devised in view of the above-described problems, and an object thereof is to provide a sensor element which has through holes penetrating the plurality of solid electrolytes in the thicknesswise direction and in which energizing paths formed by respective conductive layers disposed in the through holes are not prone to disconnection, as well as to a method of manufacturing the sensor element and a sensor including the sensor element.

SUMMARY OF THE INVENTION

In accordance with a first aspect, the above object of the present invention has been achieved by providing a sensor element comprising: a first solid electrolyte layer having a first through hole which penetrates from a first obverse surface to a first reverse surface located on a side opposite the first obverse surface; and a second solid electrolyte layer having a second through hole which penetrates from a second obverse surface to a second reverse surface located on a side opposite the second obverse surface and which connects to the first through hole, the second solid electrolyte layer being stacked on the first solid electrolyte layer by bringing the first reverse surface and the second obverse surface into contact with one another directly or through another member, the first solid electrolyte layer including a first inner insulating layer provided on an inner surface of the first through hole, a first outer insulating layer connected to the first inner insulating layer and provided on the first reverse surface, a first inner conductive layer provided on the first inner insulating layer, and a first outer conductive layer connected to the first inner conductive layer and provided on the first outer insulating layer, the second solid electrolyte layer including a second inner insulating layer provided on an inner surface of the second through hole, a second outer insulating layer connected to the second inner insulating layer and provided on the second obverse surface, a second inner conductive layer provided on the second inner insulating layer, and a second outer conductive layer connected to the second inner conductive layer and provided on the second outer insulating layer, and wherein the first outer conductive layer and the second outer conductive layer are in contact with one another.

In this sensor element, the first inner conductive layer is provided in the first through hole of the first solid electrolyte layer, and the first outer conductive layer is provided on the first reverse surface. Additionally, the second inner conductive layer is provided in the second through hole of the second solid electrolyte layer, and the second outer conductive layer is provided on the second obverse surface. In such a sensor element, the first solid electrolyte layer and the second solid electrolyte layer are stacked after appropriately forming the first inner conductive layer and the first outer conductive layer (hereafter referred to as the first conductive layer) for the first solid electrolyte layer as well as the second inner conductive layer and the second outer conductive layer (hereafter referred to the second conductive layer) for the second solid electrolyte layer. Therefore, energizing paths can be appropriately formed in both the first through hole and the second through hole (i.e., a through hole having a large lengthwise dimension) which respectively penetrate the stacked first solid electrolyte layer and second solid electrolyte layer.

Namely, since the respective lengthwise dimensions of the first through hole and the second through hole are shorter than the connected through hole in the stacked first solid electrolyte layer and second solid electrolyte layer, the operation of inserting the first conductive layer and the second conductive layer is facilitated, whereby the first conductive layer and the second conductive layer are not prone to disconnection.

Further, in stacking the first solid electrolyte layer and the second solid electrolyte layer respectively provided with the first conductive layer in the first through hole and the second conductive layer in the second through hole so as to electrically connect the first conductive layer and the second conductive layer, since the first outer conductive layer and the second outer conductive layer having greater cross-sectional areas than the first through hole and the second through hole are made to contact one another, an excellent connection state between the first conductive layer and the second conductive layer is achieved.

Consequently, an energizing path can be reliably formed in the connected through hole penetrating the stacked first solid electrolyte layer and second solid electrolyte layer.

Furthermore, the insulating layer for electrically insulating the first solid electrolyte layer and the first conductive layer, or the insulating layer for electrically insulating the second solid electrolyte layer and the second conductive layer, not only comprises the first inner insulating layer and the second inner insulating layer but also the first outer insulating layer and the second outer insulating layer. Therefore, it is possible to prevent electrical connection between the first solid electrolyte layer and the first outer conductive layer and between the second solid electrolyte layer and the second outer conductive layer. Consequently, it becomes possible to prevent short-circuiting between the first solid electrolyte layer and the first conductive layer and between the second solid electrolyte layer and the second conductive layer (particularly between the first solid electrolyte layer and the first outer conductive layer and between the second solid electrolyte layer and the second outer conductive layer), thereby making it possible to prevent breakage (such as the blackening of the first solid electrolyte layer and the second solid electrolyte layer) of the sensor element.

Furthermore, in the above-described sensor element in accordance with a second aspect of the invention, when the first solid electrolyte layer is viewed in a direction perpendicular to a thicknesswise direction thereof, the first outer insulating layer preferably extends further from a periphery of the first through hole than the first outer conductive layer, and when the second solid electrolyte layer is viewed in a direction perpendicular to a thicknesswise direction thereof, the second outer insulating layer preferably extends further from a periphery of the second through hole than the second outer conductive layer.

Thus, since the first outer insulating layer extends further than the first outer conductive layer, and the second outer insulating layer extends further than the second outer conductive layer, it is possible to more effectively prevent electrical connection between the first solid electrolyte layer and the first outer conductive layer and between the second solid electrolyte layer and the second outer conductive layer. Further, in accordance with a third aspect of the invention, the first outer insulating layer preferably extends further than the first outer conductive layer by 0.1 mm or more, and the second outer insulating layer preferably extends further than the second outer conductive layer by 0.1 mm or more.

In the above-described sensor element in accordance with a fourth aspect of the invention, the first outer insulating layer and the second outer insulating layer are preferably in contact with one another through an intermediate insulating layer.

If the first outer conductive layer and the second outer conductive layer are brought into contact with one another by causing the first outer insulating layer to extend further than the first outer conductive layer and by causing the second outer insulating layer to extend further than the second outer conductive layer, there are cases where a space is formed between the first outer insulating layer and the second outer insulating layer. By providing an intermediate insulating layer in this space, it is possible to prevent the first solid electrolyte layer and the first conductive layer and the second solid electrolyte layer and the second conductive layer from short-circuiting through this space. The intermediate insulating layer is preferably brought into contact with the first outer conductive layer and the second outer conductive layer. Consequently, the open space is not formed, and it is possible to reliably prevent short-circuiting between the first solid electrolyte layer and the first conductive layer and between the second solid electrolyte layer and the second conductive layer.

In the above-described sensor element in accordance with a fifth aspect of the invention, the first solid electrolyte layer and the second solid electrolyte layer are preferably in contact with one another through the intermediate insulating layer. The intermediate insulating layer thus formed is able to prevent the first solid electrolyte layer and the second solid electrolyte layer from coming into contact with one another.

In the sensor element having an intermediate insulating layer in accordance with a sixth aspect of the invention, an interval dimension between the first reverse surface and the second obverse surface is preferably in a range of 10 μm to 100 μm.

Namely, as the interval dimension between the first solid electrolyte layer and the second solid electrolyte layer is set to 10 μm or more, it is possible to ensure insulation between the first solid electrolyte layer and the second solid electrolyte layer.

On the other hand, if the thicknesswise dimension of the intermediate insulating layer becomes large, the rate of heat transfer through the intermediate insulating layer becomes slow, to thereby impart a temperature difference between the respective portions of the sensor element. Thus, owing to a difference in thermal expansion due to a difference in temperature, the first solid electrolyte layer and the second solid electrolyte layer can exfoliate, possibly leading to a broken sensor element. Accordingly, as the interval dimension between the first solid electrolyte layer and the second solid electrolyte layer is set to 100 μm or less, the temperature difference between the respective portions of the sensor element is suppressed, thereby making it possible to prevent breakage of the sensor element due to a difference in thermal expansion.

In the sensor element having the above-described intermediate insulating layer in accordance with a seventh aspect of the invention, it is possible to adopt an arrangement in which the first through hole and the second through hole are arranged in longitudinally rear end portions of the first solid electrolyte layer and the second solid electrolyte layer, respectively, and a heating portion is provided on a leading end portion of the sensor element, wherein the intermediate insulating layer is also provided on the leading end portion where the heating portion is located, between the first solid electrolyte layer and the second solid electrolyte layer, and wherein a thicknesswise dimension of the intermediate insulating layer at the leading end side is smaller than a thicknesswise dimension of the intermediate insulating layer at the rear end portion where the first through hole and the second through hole are located.

Thus, in the sensor element having a heating portion, the leading end portion where the heating portion is provided assumes a higher temperature as compared with the rear end portion where the first through hole and the second through hole are formed. Therefore, exfoliation of the second solid electrolyte layer and the first solid electrolyte layer with respect to the intermediate insulating layer due to a difference in thermal expansion tends to occur more frequently in the leading end portion.

On the other hand, the intermediate insulating layer has a thicknesswise dimension in the leading end portion that is smaller than its thicknesswise dimension in the rear end portion. For this reason, a temperature difference between respective portions in the thicknesswise direction is suppressed in the leading end portion (i.e., the portion where the heating portion is formed) of the sensor element as compared with the rear end portion thereof.

Hence, in accordance with the invention, even in cases where a heating portion is provided, the arrangement is such that a temperature difference at the portion where the heating portion is formed is suppressed, thereby making it possible to prevent sensor element breakage due to a difference in thermal expansion.

The leading end side of the sensor element is the side having a portion which is exposed to the gas to be detected among opposing longitudinal ends, and the rear end side of the sensor element is the side opposite the leading end side.

In the above-described sensor element in accordance with an eighth aspect of the invention, the intermediate insulating layer is preferably formed continuously from the leading end portion to the rear end portion of the sensor element between the first solid electrolyte layer and the second solid electrolyte layer, and has a dimension changing portion at which the thicknesswise dimension of the intermediate insulating layer changes so as to become smaller on a leading end portion side of the dimension changing portion.

Since the intermediate insulating layer is provided with the dimension changing portion, it is possible to easily realize an intermediate insulating layer in which the thicknesswise dimension at the leading end portion differs from the thicknesswise dimension at the rear end portion.

The dimension changing portion of the intermediate insulating layer may be formed in a stepped shape in which the thicknesswise dimension changes in steps along the longitudinal direction of the sensor element, or may be formed in a tapered shape in which the thicknesswise dimension changes gradually along the longitudinal direction of the sensor element.

Furthermore, the above-described sensor element in accordance with a ninth aspect of the invention may further comprise: a third outer insulating layer provided on the first obverse surface and connected to the first inner insulating layer and a third outer conductive layer which is provided on the third outer insulating layer and which is connected to the first inner conductive layer, and a chamfered portion provided on a longitudinally rear end side of the first solid electrolyte layer, the third outer insulating layer being exposed at a surface of the chamfered portion.

In a case where the first solid electrolyte layer is an outermost layer, the chamfering portion is formed for preventing breakage of a corner portion of the sensor element. In addition, there are cases where the third outer insulating layer for establishing electrical contact with an external circuit is formed on the first obverse surface of the first solid electrolyte layer. In this case, since the third outer insulating layer is formed at the chamfered portion, it is possible to reliably prevent short-circuiting between the first solid electrolyte layer and the third outer conductive layer.

Next, to attain the above object, in accordance with a tenth aspect, the present invention provides a method of manufacturing a sensor element including a first solid electrolyte layer having a through hole which penetrates from a first obverse surface to a first reverse surface located on a side opposite the first obverse surface; and a second solid electrolyte layer having a through hole which penetrates from a second obverse surface to a second reverse surface located on a side opposite the second obverse surface and which connects to the first through hole, the second solid electrolyte layer being stacked on the first solid electrolyte layer by bringing the first reverse surface and the second obverse surface into contact with one another directly or through another member, comprising the steps of: an insulating-layer forming step which comprises forming a first inner insulating layer on an inner surface of the first through hole of the first solid electrolyte layer before stacking, forming on the first reverse surface a first outer insulating layer which is connected to the first inner insulating layer, forming a second inner insulating layer on an inner surface of the second through hole of the second solid electrolyte layer, and forming a second outer insulating layer which is connected to the second inner insulating layer on the second obverse surface; a conductive-layer forming step which comprises forming a first inner conductive layer on the first inner insulating layer, forming on the first outer insulating layer a first outer conductive layer which is connected to the first inner conductive layer, forming a second inner conductive layer on the second inner insulating layer, and forming on the second outer insulating layer a second outer conductive layer which is connected to the second inner conductive layer; and a stacking step which comprises stacking the first solid electrolyte layer and the second solid electrolyte layer while the first outer conductive layer and the second outer conductive layer are brought into contact with one another.

Thus, since the insulating layers including the first inner insulating layer, the first outer insulating layer, the second inner insulating layer, and the second outer insulating layer are formed in the insulating-layer forming step, after the first conductive layer and the second conductive layer are formed in the subsequent conductive-layer forming step, the insulating layers can prevent the first conductive layer and the second conductive layer from coming into contact with the first solid electrolyte layer and the second solid electrolyte layer. In this manner, it is possible to manufacture a sensor element which prevents short-circuiting between the first conductive layer or the second conductive layer and the first solid electrolyte layer or the second solid electrolyte layer.

In addition, in this method of manufacturing a sensor element, after the first conductive layer and the second conductive layer are respectively formed for the first solid electrolyte layer and the second solid electrolyte layer in the conductive-layer forming step, the first solid electrolyte layer and the second solid electrolyte layer are stacked while the first outer conductive layer and the second outer conductive layer are brought into contact with one another in the stacking step. Thus, since the first conductive layer and the second conductive layer are inserted into the first through hole of the first solid electrolyte layer and the second through hole of the second solid electrolyte layer (i.e., into the through holes whose lengthwise dimension is small), the operation of inserting the conductive members is facilitated.

Hence, according to the method of manufacturing a sensor element in accordance with the invention, it is possible to manufacture a sensor element which prevents short-circuiting between the first conductive layer and the first solid electrolyte layer and between the second conductive layer and the second solid electrolyte layer, and in which the first conductive layer and the second conductive layer are reliably connected.

Next, to attain the above object, in accordance with an eleventh aspect, the present invention provides a gas sensor comprising: a detecting element extending in an axial direction and having a leading end portion directed toward a gas to be measured; a metal shell which surrounds a periphery of the detecting element in which the leading end portion and a rear end portion of the detecting element project from opposite ends of the metal shell; and a supporting member disposed between the detecting element and the metal shell for supporting the detecting element in the metal shell, wherein the detecting element is the sensor element according to any one of the first to ninth aspects of the invention.

Since this gas sensor has a detecting element constituted by the sensor element according to any one of the first to ninth aspects, the reliability of the energizing paths through the through holes in the interior of the detecting element is improved, so that it is possible to suppress a decrease in gas detection accuracy attributable to faulty energizing paths and to prevent a deterioration in the gas detection accuracy of the sensor.

DESCRIPTION OF REFERENCE NUMERALS

Figure 1:
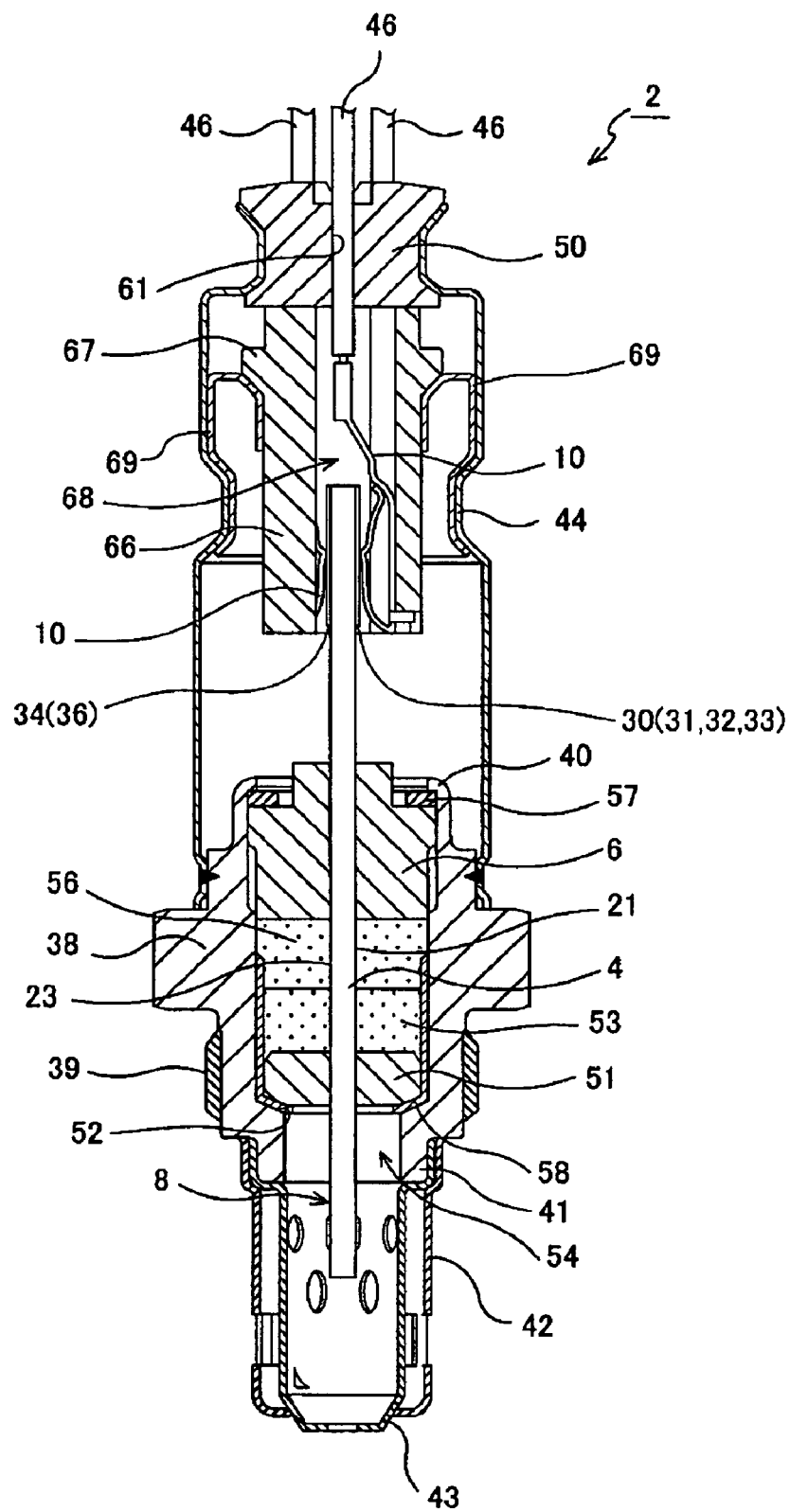
FIG. 1 is a cross-sectional view illustrating the overall configuration of an $NO_x$ sensor.

Reference numerals used to identify various structural features in the drawings include the following.

2: $NO_x$ sensor, 4: gas sensor element, 10: leadframe (connection terminal), 20: detecting element, 22: heater, 30, 31, 32, 33, 34 and 36: electrode terminal portions, 37: outer intermediate insulating layer, 38: metal shell, 69: holding member, 121: heating resistor pattern, 123: third solid electrolyte substrate, 125: second solid electrolyte substrate, 127: first solid electrolyte substrate, 129: inner intermediate insulating layer, 131: heating portion, 133: second through hole, 134: first through hole, 135: heater lead portion, 137: first conductive layer, 138: second conductive layer, 204: second sensor element, 222: second heater, 229: second inner intermediate insulating layer, 230, 330: dimension changing portion, 304: third sensor element, 322: third heater, 329: third inner intermediate insulating layer, 404: fourth sensor element, 500: chamfered portion

DETAILED DESCRIPTION OF THE INVENTION

Hereafter, a description will be given of an embodiment of the invention with reference to the accompanying drawings. However, the present invention should not be construed as being limited thereto.

As an embodiment of the invention, a description will be given of an $NO_x$ sensor 2 which is installed in an exhaust pipe of an internal combustion engine to detect $NO_x$ contained in exhaust gas.

The $NO_x$ sensor 2 is a type of gas sensor having a configuration comprising a detecting element (gas sensor element) for detecting a particular component of exhaust gas subject to measurement in an automobile or various internal combustion engines.

(1) Configuration of the Overall $NO_x$ Sensor

FIG. 1 is a cross-sectional view illustrating the overall configuration of the $NO_x$ sensor 2 in accordance with an embodiment of the invention.

The $NO_x$ sensor 2 is comprised of a cylindrical metal shell 38 having a threaded portion 39 formed on its outer surface for fixing to an exhaust pipe; a gas sensor element 4 formed in the shape of a plate and extending in an axial direction (in the longitudinal direction of the $NO_x$ sensor 2, i.e., in the vertical direction in the drawing); a cylindrical ceramic sleeve 6 which is disposed so as to surround the radial periphery of the gas sensor element 4; an insulating contact member 66 which is disposed in a state in which the inner wall surface of a contact insertion hole 68 penetrating in the axial direction surrounds a rear end portion of the gas sensor element 4; and a plurality of (only two are shown in FIG. 1) contact terminals 10 (the leadframe 10) which are disposed between the gas sensor element 4 and the insulating contact member 66.

The gas sensor element 4 has the shape of an elongated plate extending in the axial direction, and has a detecting portion 8 formed on the leading end side (a lower side in the drawing, i.e., an axially distal end portion) which is directed toward the gas to be measured. Further, the gas sensor element 4 has electrode terminal portions 30, 31, 32, 33, 34 and 36 formed on a first outer portion 21 and a second outer portion 23 which assume a positional relationship of two sides on the outer surface of the rear end side (an upper side in the drawing, i.e., an axially rear end portion).

The connection terminals 10 are respectively electrically connected to the electrode terminal portions 30, 31, 32, 33, 34 and 36 of the gas sensor element 4 by disposing the connection terminals 10 between the gas sensor element 4 and the insulating contact members 66. In addition, the connection terminals 10 are also electrically connected to lead wires 46 disposed in the interior of the sensor from outside the sensor, so as to form current paths between an external device, to which the lead wires 46 are connected, and the electrode terminal portions 30, 31, 32, 33, 34 and 36.

The metal shell 38 is configured substantially in the shape of a cylinder which has a through hole 54 penetrating the metal shell in the axial direction and has a stepped portion 52 projecting radially inwardly of the through hole 54. In addition, the metal shell 38 is constructed so as to hold the gas sensor element 4 inserted in the through hole 54 in a state in which the detecting portion 8 is disposed outside the leading end side of the through hole 54, while the electrode terminal portions 30, 31, 32, 33, 34 and 36 are disposed outside the rear end side of the through hole 54. Further, the stepped portion 52 is formed as an inwardly oriented tapered surface inclined with respect to a plane perpendicular to the axial direction.

A ceramic holder 51 having an annular shape, powder filler layers 53 and 56 (hereafter, also referred to as talc rings 53 and 56), and the aforementioned ceramic sleeve 6 are stacked in that order from the leading end side toward the rear end side inside the through hole 54 of the metal shell 38 so as to surround the radial periphery of the gas sensor element 4. In addition, a crimp packing 57 is disposed between the ceramic sleeve 6 and a rear end portion 40 of the metal shell 38, and a metal holder 58 for holding the talc ring 53 and the ceramic holder 51 is disposed between the conductive layer 51 and the stepped portion 52 of the metal shell 38. The rear end portion 40 of the metal shell 38 is crimped so as to press the ceramic sleeve 6 toward the leading end side through the crimp packing 57.

In addition, a protector having a dual structure (consisting of an outer protector 42 and an inner protector 43 which will be described below) made of a metal (e.g., stainless steel) for covering the projecting portion of the gas sensor element 4 is attached to an outer periphery of a leading end portion 41 of the metal shell 38 by welding or the like.

An outer cylinder 44 is fixed to an outer periphery on the rear end side of the metal shell 38. In addition, a grommet 50 is disposed at an opening on the rear end side (upper side in FIG. 1) of the outer cylinder 44. A lead wire insertion hole 61, into which the six lead wires 46 (only three lead wires are shown in FIG. 1, which lead wires 46 are respectively electrically connected to the electrode terminal portions 30, 31, 32, 33, 34 and 36 of the gas sensor element 4) are inserted, is formed in the grommet 50.

The insulating contact member 66 is disposed on the rear end side (upper side in FIG. 1) of the gas sensor element 4 projecting from the rear end portion 40 of the metal shell 38. The insulating contact member 66 is disposed around the electrode terminal portions 30, 31, 32, 33, 34 and 36 formed on the rear end surface of the gas sensor element 4. A projecting portion 67 is formed on the insulating contact member 66, and the projecting portion 67 is fixed to the outer cylinder 44 through a holding member 69.

The ceramic sleeve 6, the ceramic holder 51, and the talc rings 53 and 56 correspond to the supporting members referred in the summary of the invention.

(2) Configuration of the Gas Sensor Element 4

Figure 2:
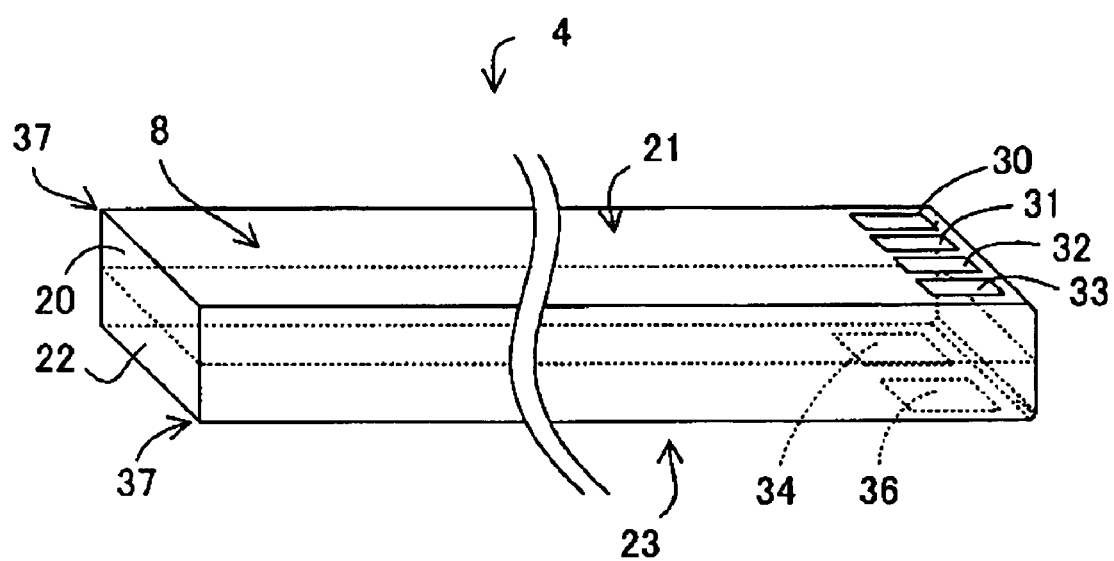
FIG. 2 is a perspective view illustrating a schematic structure of a gas sensor element.

Here, a perspective view illustrating a schematic structure of the gas sensor element 4 is shown in FIG. 2. In FIG. 2, the gas sensor element 4 is shown as omitting an axially intermediate portion.

The gas sensor element 4 is comprised of a detecting element 20, a heater 22, an outer intermediate insulating layer 37, and the electrode terminal portions 30, 31, 32, 33, 34 and 36. The rough configuration of the gas sensor element 4 provided in the $NO_x$ sensor 2 is as follows.

First, as the detecting element 20 formed in the shape of a plate extending in the axial direction (in the left-right direction in FIG. 2) and the heater 22 similarly formed in the shape of a plate extending in the axial direction are stacked, the gas sensor element 4 assumes the shape of a plate having a rectangular axial cross section.

Further, since the detecting element 20 for detecting $NO_x$ is conventionally known, a detailed description of its internal structure and the like will be omitted, but its rough configuration is as follows.

The detecting element 20 is comprised of an oxygen concentration detecting cell in which porous electrodes are formed on both sides of a solid electrolyte substrate (plate-like substrate formed of a solid electrolyte body); an oxygen pump cell similarly having porous electrodes formed on both sides of a solid electrolyte substrate; an $NO_x$ cell similarly having porous electrodes formed on both sides of a solid electrolyte substrate; and spacers which are stacked between these elements and form a hollow measurement gas chamber.

This solid electrolyte substrate is formed of zirconia in which yttria is solidly dissolved as a stabilizer. The porous electrodes are composed principally of Pt. In addition, the spacers for forming the measurement gas chamber are constituted mainly of alumina. The spaces are disposed such that one porous electrode in the oxygen concentration detection cell and one porous electrode in the oxygen pump cell are exposed inside a hollow measurement gas chamber.

The measurement gas chamber is provided as an internal space on the leading end side of the detecting element 20. Further, in the detecting element 20, a region where the measurement gas chamber, the porous electrodes, and the like are formed is the detecting portion 8 of the gas sensor element 4.

In addition, a diffusion controlling portion (not shown) allowing the measurement gas chamber and the outside of the detecting element 20 to communicate with one another is formed in the detecting element 20. This diffusion controlling portion is constituted of, for example, a porous body formed of alumina or the like and is rate controlling when the gas to be measured flows into the measurement gas chamber. Further, a ventilation portion (not shown) constituted of a porous body is formed in the detecting element 20. This ventilation portion is used for the passage of oxygen which moves due to the driving of the oxygen pump cell.

In the detecting element 20 in accordance with this embodiment, the electrode terminal portions 30, 31, 32 and 33 are electrically connected to the porous electrodes of the oxygen concentration detecting cell and the porous electrodes of the oxygen pump cell which are provided in the detecting element 20, by means of through hole conductors (not shown) disposed in through holes (not shown) which penetrate and are connected in the stacking direction of the detecting element 20. Since an intermediate insulating layer constituted of an insulating material is formed on an inner peripheral surface of each connecting through hole, the through hole conductor is not in direct contact with the solid electrolyte substrate but is connected to the porous electrode of each cell through a wiring portion and the like.

Figure 3:
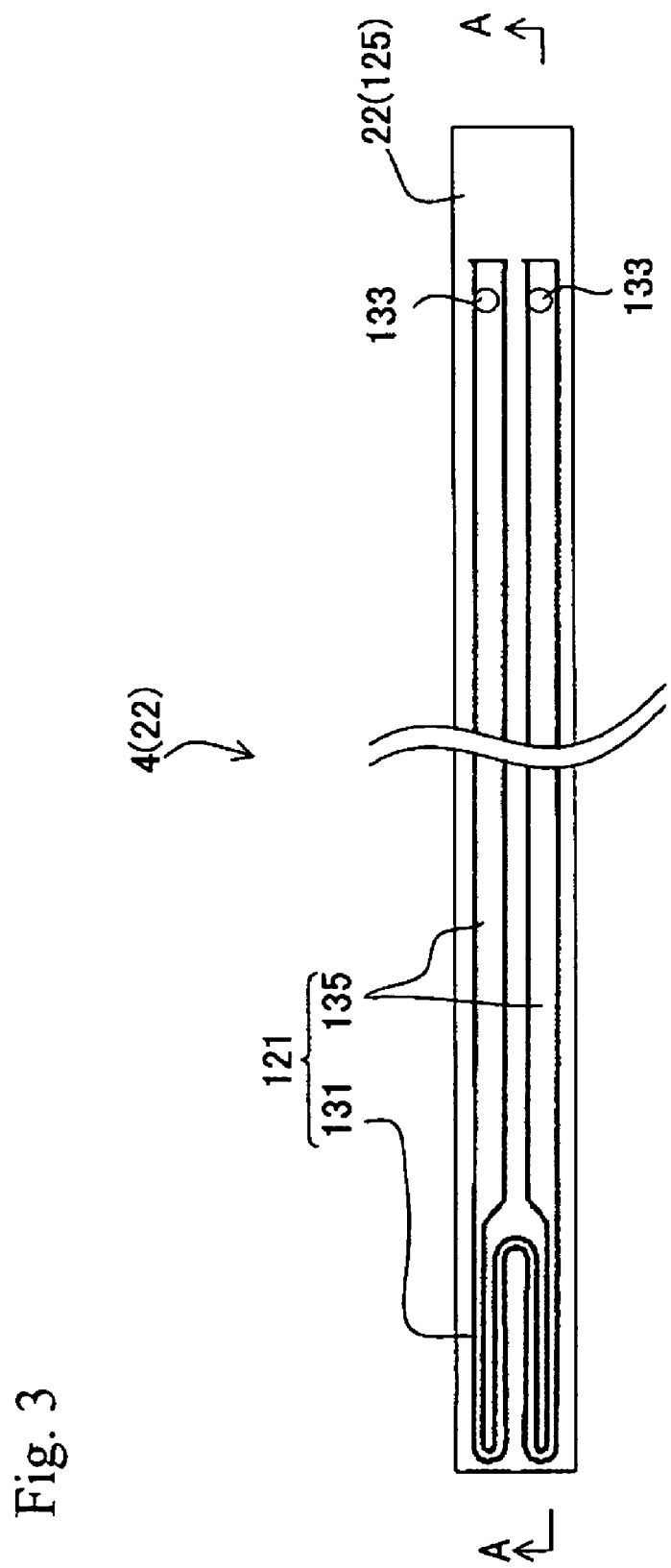
FIG. 3 is a cross-sectional view illustrating the internal structure on a stacking surface where a heating resistor pattern of a heater in the gas sensor element is formed.
Figure 4:
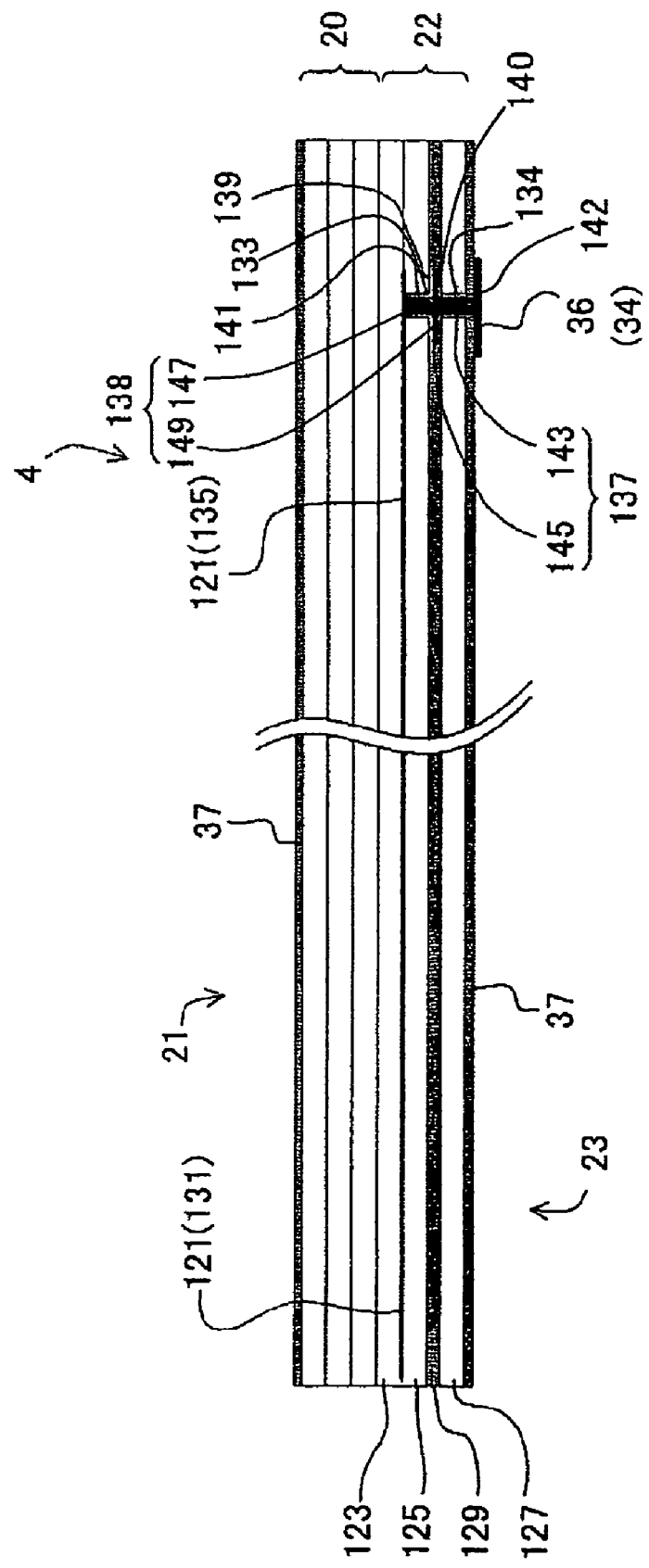
FIG. 4 is a cross-sectional view, taken along line A-A in FIG. 3, of the internal structure of the gas sensor element.
Figure 5:
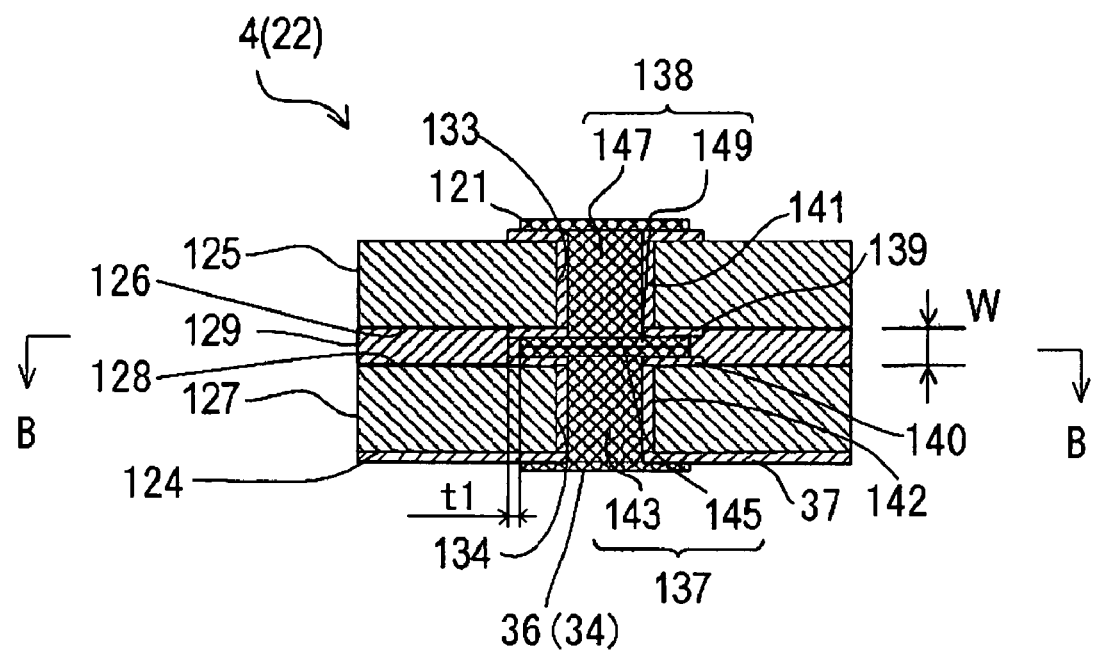
FIG. 5 is an explanatory diagram in which a first solid electrolyte substrate, a second solid electrolyte substrate, and an inner intermediate insulating layer are stacked.

Next, FIG. 3 shows a cross-sectional view illustrating the internal structure on a stacking surface where a heating resistor pattern 121 of the heater 22 in the gas sensor element 4 is formed. FIG. 4 shows a cross-sectional view, taken along line A-A in FIG. 3, of the internal structure of the gas sensor element 4. In FIG. 4, the internal structure of the detecting element 20 is not shown. Further, FIG. 5 is an enlarged explanatory diagram of the through hole portions of a second solid electrolyte substrate 125, a first solid electrolyte substrate 127, and an inner intermediate insulating layer 129 shown in FIG. 4, and illustration of the detecting element 20 is omitted. In FIGS. 3, 4 and 5, the gas sensor element 4 is shown as omitting an axially intermediate portion.

The heater 22 is comprised of the heating resistor pattern 121 composed principally of Pt; three solid electrolyte substrates 123, 125 and 127 composed principally of zirconia; the inner intermediate insulating layer 129 composed principally of alumina; the pair of electrode terminal portions 34 and 36 for connecting to an external circuit; and two pairs of a first conductive layer 137 and a second conductive layer 138 (one pair is shown in FIGS. 4 and 5) composed principally of an electrically conductive material.

The three solid electrolyte substrates 123, 125 and 127 are formed in the shape of a plate extending in the longitudinal direction, and are arranged in the order of the third solid electrolyte substrate 123, the second solid electrolyte substrate 125, and the first solid electrolyte substrate 127 in the direction from the first outer portion 21 toward the second outer portion 23 of the gas sensor element 4. Further, two pairs of a second through hole 133 and a first through hole 134 (one pair is shown in FIGS. 4 and 5), which penetrate in the thicknesswise direction of the outer portion on the rear end side, are respectively formed in the second solid electrolyte substrate 125 and the first solid electrolyte substrate 127.

As shown in FIG. 4, the heating resistor pattern 121 is formed between the third solid electrolyte substrate 123 and the second solid electrolyte substrate 125. Additionally, as shown in FIG. 3, the heating resistor pattern 121 includes a heating portion 131 provided on a longitudinally leading end side (the left-hand side is the leading end side in FIG. 3) of the heater 22, as well as a pair of heater lead portions 135 respectively extending toward the rear end side (the right-hand side is the leading end side in FIG. 3) from both end portions of the heating portion 131. The pair of heater lead portions 135 are respectively formed so as to extend from the end portions of the heating portions 131 toward the second through holes 133.

Further, the intermediate insulating layer (not shown) is formed between the heating resistor pattern 121 and the third solid electrolyte substrate 123 or between the heating resistor pattern 121 and the second solid electrolyte substrate 125.

The second solid electrolyte substrate 125 and the first solid electrolyte substrate 127 are stacked with the inner intermediate insulating layer 129 interposed therebetween, and the outer intermediate insulating layer 37 is formed on an outer surface of the first solid electrolyte substrate 127. The two pairs of the second through hole 133 and the first through hole 134 respectively formed in the second solid electrolyte substrate 125 and the first solid electrolyte substrate 127 are connected to the through hole 136 of the inner intermediate insulating layer 129 (see FIG. 6), to thereby form connected through holes penetrating the second solid electrolyte substrate 125, the inner intermediate insulating layer 129, and the first solid electrolyte substrate 127 in their stacking direction.

As shown in FIG. 5, the first conductive layer 137 and the second conductive layer 138, which are respectively provided in the first through hole 134 of the first solid electrolyte substrate 127 and the second through hole 133 of the second solid electrolyte substrate 125, are connected to one another to thereby form a conduction path leading from one end to the other end of the connected through holes.

A second outer insulating layer 139 is formed on a peripheral edge of the second through hole 133 in a second obverse surface 126 of the second solid electrolyte substrate 125. Further, a second inner insulating layer 141 is formed on an inner surface of the second through hole 133 of the second solid electrolyte substrate 125. Meanwhile, a first outer insulating layer 140 is formed on a peripheral edge of the first through hole 134 in a first reverse surface 128 of the first solid electrolyte substrate 127. Further, a first inner insulating layer 142 is formed on an inner surface of the first through hole 134 of the first solid electrolyte substrate 127.

In addition, the first conductive layers 137 and the second conductive layers 138 are respectively provided in the first through holes 134 and the second through holes 133 and electrically connect the heating resistor pattern 121 and the electrode terminal portions 34 and 36.

Specifically, the first conductive layer 137 has a first inner conductive layer 143 and a first outer conductive layer 145. Of these, the first inner conductive layer 143 is disposed in the first through hole 134 (on the first inner insulating layer 142) in the first solid electrolyte substrate 127. Meanwhile, the first outer conductive layer 145 is electrically connected to the first inner conductive layer 143 and is formed on the first outer insulating layer 140.

In addition, the second conductive layer 138 has a second inner conductive layer 147 and a second outer conductive layer 149. Of these, the second inner conductive layer 147 is disposed in the second through hole 133 (on the second inner insulating layer 141) in the second solid electrolyte substrate 125. Meanwhile, the second outer conductive layer 149 is electrically connected to the second inner conductive layer 147 and is formed on the second outer insulating layer 139.

Thus, in the sensor element 4 (heater 22), the first inner conductive layer 143 is provided in the first through hole 134 of the first solid electrolyte substrate 127, and the first outer conductive layer 145 is provided on the first reverse surface 128. Additionally, the second inner conductive layer 147 is provided in the second through hole 133 of the second solid electrolyte substrate 125, and the second outer conductive layer 149 is provided on the second obverse surface 126. In such a sensor element 4, the first solid electrolyte substrate 127 and the second solid electrolyte substrate 125 are stacked after appropriately forming the first inner conductive layer 143 and the first outer conductive layer 145 for the first solid electrolyte substrate 127 and the second inner conductive layer 147 and the second outer conductive layer 149 for the second solid electrolyte substrate 125. In this manner, energizing paths can be appropriately formed in both the first through holes 134 and the second through holes 133 which respectively penetrate the stacked first solid electrolyte substrate 127 and second solid electrolyte substrate 125.

Further, the first solid electrolyte substrate 127 and the second solid electrolyte substrate 125 respectively provided with the first conductive layer 137 in the first through hole 134 and the second conductive layer 138 in the second through hole 133 are stacked so as to electrically connect the first conductive layer 137 and the second conductive layer 138. Consequently, since the first outer conductive layer 145 and the second outer conductive layer 149 having a greater cross-sectional area than the first through hole 134 and the second through hole 133, respectively, are aligned to contact one another, an excellent state of connection between the first conductive layer 137 and the second conductive layer 138 is secured.

In addition, the insulating layer for electrically insulating the first solid electrolyte substrate 127 and the first conductive layer 137, or the insulating layer for electrically insulating the second solid electrolyte substrate 125 and the second conductive layer 138, includes not only the first inner insulating layer 142 and the second inner insulating layer 141 but also the first outer insulating layer 140 and the second outer insulating layer 139. Therefore, by employing this structure, it is possible to prevent electrical connection between the first solid electrolyte substrate 127 and the first outer conductive layer 145 and between the second solid electrolyte substrate 125 and the second outer conductive layer 149.

In addition, the first outer insulating layer 140 laterally projects (i.e., extends in a lateral direction) further from a periphery of the first through hole than the first outer conductive layer 145. Further, the second outer insulating layer 139 laterally projects further from a periphery of the second through hole than the second outer conductive layer 149. Specifically, the distance between projecting edge portions of the first outer insulating layer 140 and the second outer insulating layer 139 is set to 0.2 mm.

Thus, since the first outer insulating layer 140 projects further than the first outer conductive layer 145, and since the second outer insulating layer 139 projects further than the second outer conductive layer 149, it is possible to more surely prevent electrical connection between the first solid electrolyte substrate 127 and the first outer conductive layer 145 and between the second solid electrolyte substrate 125 and the second outer conductive layer 149.

Further, the inner intermediate insulating layer 129 is formed at the projecting portions of the first outer insulating layer 140 and the second outer insulating layer 139. As a result, the gap between the first outer insulating layer 140 and the second outer insulating layer 130 can be filled, so that it is possible to prevent short-circuiting between the first solid electrolyte substrate 127 and the first conductive layer 137 through a space which is otherwise formed, and to prevent short-circuiting between the second solid electrolyte substrate 125 and the second conductive layer 138 through a space which is otherwise formed.

Furthermore, as shown in FIG. 4, the inner intermediate insulating layer 129 is in contact with the first solid electrolyte substrate 127 and the second solid electrolyte substrate 125. Consequently, it is possible to prevent mutual contact between the first solid electrolyte substrate 127 and the second solid electrolyte substrate 125.

Furthermore, the interval dimension W between the first reverse surface 128 and the second obverse surface is 50 μm. When the interval dimension W between the first solid electrolyte substrate 127 and the second solid electrolyte substrate 125 is set to 10 μm or more, it is possible to ensure electrical insulation between the first solid electrolyte substrate 127 and the second solid electrolyte substrate 125. In addition, when the interval dimension W between the first solid electrolyte substrate 127 and the second solid electrolyte substrate 125 is set to 100 μm or less, it becomes difficult to impart a temperature difference between the respective portions of the sensor element 4, thereby making it possible to prevent breakage of the sensor element 4 due to a difference in thermal expansion.

Next, as shown in FIG. 4, the outer intermediate insulating layer 37 is formed so as to cover at least rear end portions of the first outer portion 21 and the second outer portion 23 of the solid electrolyte substrates constituting the detecting element 20 and the heater 22. The outer intermediate insulating layer 37 is constituted of an insulating material composed principally of alumina.

As shown in FIG. 2, the gas sensor element 4 has four electrode terminal portions 30, 31, 32 and 33 on the rear end side (right-hand side in FIG. 2) of the first outer portion 21, and has the two electrode terminal portions 34 and 36 on the rear end side of the second outer portion 23.

Of these, the electrode terminal portions 30, 31, 32 and 33 are stacked on the outer intermediate insulating layer 37 formed on the first outer portion 21 of the detecting element 20, while the electrode terminal portions 34 and 36 are stacked on the outer intermediate insulating layer 37 formed on the second outer portion 23 of the heater 22. Further, as shown in FIG. 4, the electrode terminal portions 34 and 36 are electrically connected to the heating resistor pattern 121 through the first and second conductive layers 137, 138 of the heater 22.

In the case where the gas sensor element 4 is assembled to the $NO_x$ sensor 2, as described above, the electrode terminal portions 30, 31, 32, 33, 34 and 36 are connected to the contact terminals 10. Namely, the electrode terminal portions 30, 31, 32, 33, 34 and 36 are provided to constitute portions of energizing paths for connecting the interior of the gas sensor element 4 (such as the oxygen concentration detecting cell, the oxygen pump cell, the $NO_x$ cell, and the heating resistor pattern) and an external device.

(3) Method of Manufacturing the Gas Sensor Element 4

Next, the method of manufacturing the gas sensor element 4 will be described.

First, an unsintered stacked body which serves as the gas sensor element 4 after sintering is fabricated.

The unsintered stacked body is formed by stacking predetermined materials.

The predetermined materials constituting the unsintered stacked body may include unsintered solid electrolyte sheets serving as the solid electrolyte substrates of the heater 22 after sintering, as well as unsintered insulating sheets serving as the outer intermediate insulating layer 37 and the inner intermediate insulating layer 129 after sintering. Although unsintered insulating sheets are used in this embodiment, the respective parts may be formed by applying a paste to the respective unsintered solid electrolyte sheets.

Of these, each of the unsintered solid electrolyte sheets is fabricated, for example, by adding an alumina powder and a butyral resin to a ceramic powder composed principally of zirconia and mixing with a mixed solvent (toluene and methyl ethyl ketone) to produce a slurry, and by shaping the slurry into a sheet form using a doctor blade method and then by volatizing the mixed solvent.

Further, as for the unsintered solid electrolyte sheets for which through holes are required, a through-hole forming step is carried out for forming through holes at predetermined through-hole forming positions. At this time, the first through holes 134 and the second through holes 133 are respectively formed in the unsintered solid electrolyte sheets serving as the first solid electrolyte substrate 127 and the second solid electrolyte substrate 125 of the heater 22.

Next, an insulating-layer forming step is carried out for forming insulating layers on the unsintered solid electrolyte sheets at predetermined forming positions.

Specifically, as for the unsintered solid electrolyte sheets serving as the first solid electrolyte substrate 127 and the second solid electrolyte substrate 125 of the heater 22, the first inner insulating layer 142 and the second inner insulating layer 141 are respectively formed on the inner surfaces of the first through hole 134 and the second through hole 133. Additionally, the first outer insulating layer 140 and the second outer insulating layer 139 are respectively formed on the first reverse surface 128 and the second obverse surface 126 at the peripheral edges of the first through hole 134 and the second through hole 133 in the unsintered solid electrolyte sheets.

These insulating layers can be formed by printing an insulating paste composed principally of alumina by a known printing technique (such as screen printing) and by drying the printed paste. For example, at the time of printing the insulating paste, by depressurizing the through hole interiors from the through hole openings in the outer portion opposite to the printing-side outer portion in the unsintered solid electrolyte sheet, it is possible to apply the insulating paste to the inner surfaces of the through holes and to the through hole peripheral edges on the outer portion.

Next, a conductive-layer forming step is carried out for forming unsintered conductor portions on the inner surfaces of the first through holes 134 and the second through holes 133 as well as the through hole peripheral edges on the second reverse surface 126 and the first obverse surface 128. The unsintered conductor portions serve as the first conductive layer 137 and the second conductive layer 138 after sintering.

Namely, in the conductive-layer forming step, in the unsintered solid electrolyte sheet with the first through holes 134 formed therein, the first inner conductive layer 143 is formed on the first inner insulating layer 142 in the first through hole 134, and the first outer conductive layer 145, which is electrically connected to the first inner conductive layer 143 and is provided on the first outer insulating layer 140, is then formed. In addition, in the unsintered solid electrolyte sheet with the second through holes 133 formed therein, the second inner conductive layer 147 is formed on the second inner insulating layer 141 in the second through hole 133, and the second outer conductive layer 149, which is electrically connected to the second inner conductive layer 147 and is provided on the second outer insulating layer 139, is then formed.

Next, a stacking step for fabricating an unsintered stacked body is carried out. The plurality of unsintered solid electrolyte sheets with the unsintered conductive layers formed therein are stacked together with the unsintered insulating sheets and the unsintered detecting element.

Figure 6:
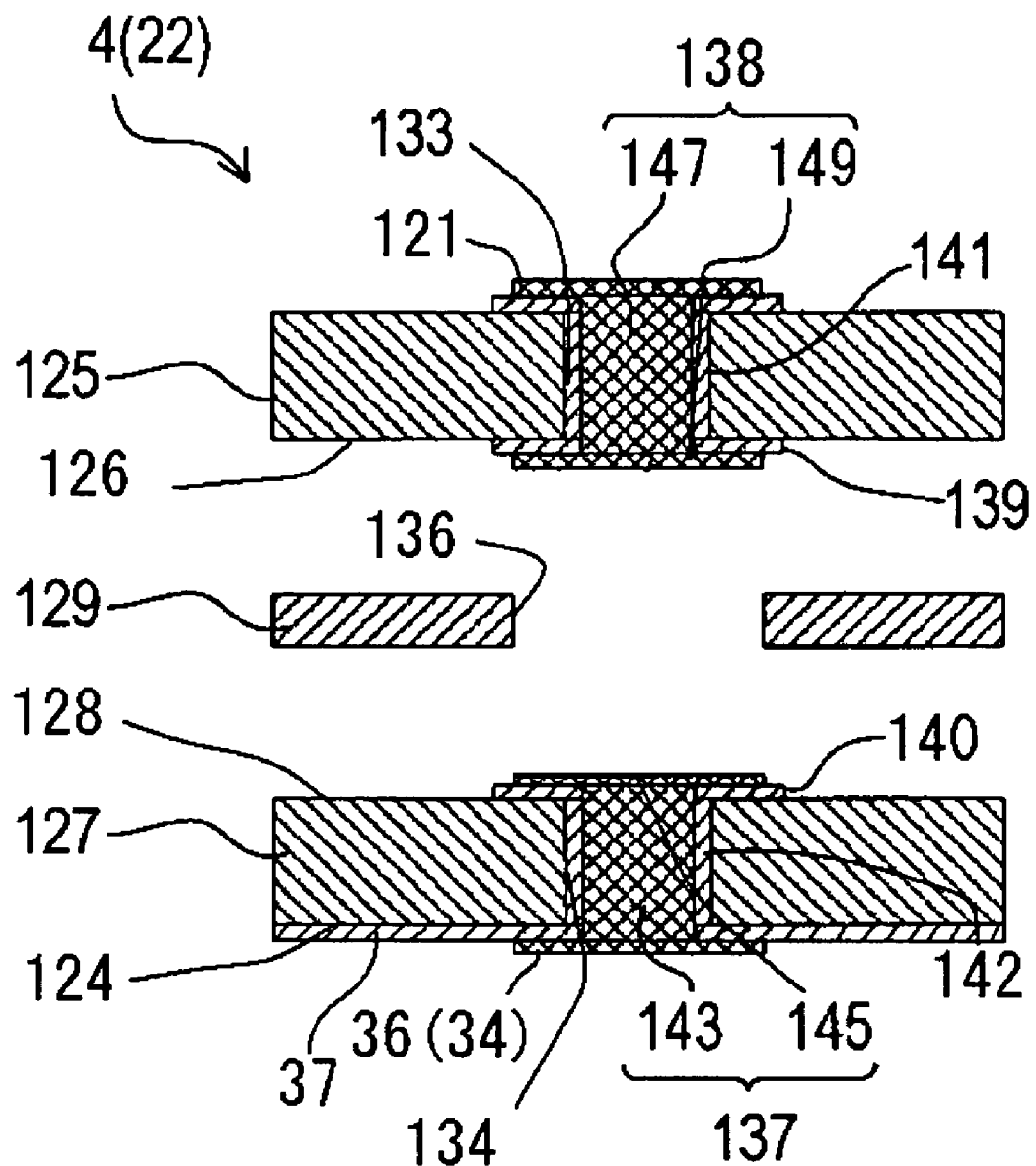
FIG. 6 is an explanatory diagram illustrating a state in which connected through holes and conductive members are formed in the step of stacking the first solid electrolyte substrate, the second solid electrolyte substrate, and the inner intermediate insulating layer.

FIG. 6 shows an explanatory diagram in which the first through hole 134 and the second through hole 133 are connected in the step of stacking the second solid electrolyte substrate 125, the third solid electrolyte substrate 127, and the inner intermediate insulating layer 129.

FIG. 6 is an explanatory diagram in which the through hole portions of the second solid electrolyte substrate 125, the third solid electrolyte substrate 127, and the inner intermediate insulating layer 129 are enlarged, and illustration of the detecting element 20 is omitted.

In the stacking step, the first through hole 134 and the second through hole 133 are connected. In this regard, the unsintered solid electrolyte sheets serving as the second solid electrolyte substrate 125 and the first solid electrolyte substrate 127 are stacked while bringing the first outer conductive layer 145 and the second outer conductive layer 149 into contact with one another. Namely, as the plurality of unsintered solid electrolyte sheets are stacked, a connected through hole (i.e., a through hole having a larger lengthwise dimension) penetrating the plurality of unsintered solid electrolyte sheets is formed, and the first conductive layer 137 and the second conductive layer 138 are connected so as to extend through the connected through hole having the larger lengthwise dimension.

In the stacking step, the unsintered stacked body may be formed by stacking all the constituent elements (such as the unsintered solid electrolyte sheets, the unsintered insulating sheets, and the unsintered detecting element) at one time, or the unsintered stacked body may be formed by stacking the respective constituent elements in accordance with a predetermined order.

In addition, the unsintered insulating sheet is fabricated by adding a butyral resin and dibutyl phthalate to a ceramic powder composed principally of zirconia and mixing with a mixed solvent (toluene and methyl ethyl ketone) to produce a slurry, and by shaping the slurry into a sheet form using a doctor blade method and then by volatizing the mixed solvent. Alternatively, instead of using the unsintered insulating sheet, the unsintered intermediate insulating layer may be formed by printing an insulating paste by a known printing technique (such as screen printing) and by drying the paste. Unsintered insulating sheets are provided as the outer intermediate insulating layer 37 and the inner intermediate insulating layer 129 after sintering.

After stacking all the predetermined materials (constituent elements) in the above-described manner, a pressurizing step is executed for obtaining a pressure-bonded unsintered stacked body by pressurizing the stacked body at a predetermined pressure (e.g., 1 Mpa). Then, the unsintered stacked body obtained in the pressurizing step is cut into predetermined sizes to thereby obtain a plurality of (e.g., 10) unsintered stacked bodies substantially conforming to the size of the gas sensor element 4.

Subsequently, a deresination step is executed for deresinating the unsintered stacked body. Further, a sintering step is executed for a predetermined duration (e.g., 1 hour) at a predetermined sintering temperature (e.g., 1500° C.) to thereby fabricate a sintered stacked body.

By executing the various steps including the aforementioned steps, a sintered stacked body is fabricated as the gas sensor element 4.

To fabricate the $NO_x$ sensor 2 using the gas sensor element 4 thus fabricated, an assembly step for assembling the gas sensor element 4 to the metal shell 38 is carried out.

Namely, in the assembly step, the gas sensor element 4 fabricated in the above-described manufacturing method is inserted into the metal holder 58, and the gas sensor element 4 is fixed by the ceramic holder 51 and the talc ring 53, thereby forming a subassembly. Subsequently, this subassembly is fixed to the metal shell 38, and while an axially rear end portion of the gas sensor element 4 is being inserted into the talc ring 56 and the ceramic sleeve 6, these portions are inserted into the metal shell 38. Then, the ceramic sleeve 6 is crimped at the rear end portion 40 of the metal shell 38, thereby fabricating a lower assembly. The outer protector 42 and the inner protector are fitted in advance to the lower assembly.

Meanwhile, an upper assembly is fabricated, for example, by assembling the outer cylinder 44, the insulating contact member 66, and the grommet 50. Then, the $NO_x$ sensor 2 can be obtained by joining the lower assembly and the upper assembly.

As described above, in the method of manufacturing the gas sensor element 4 which is provided in the $NO_x$ sensor 2, in the insulating-layer forming step, insulating layers including the first inner insulating layer 142, the second inner insulating layer 141, the first outer insulating layer 140, and the second outer insulating layer 139 are formed for the first through holes 134 in the first solid electrolyte substrate 127 and the second through holes 133 in the second solid electrolyte substrate 125. Then, in the conductive-layer forming step which is executed after the insulating-layer forming step, the first inner conductive layer 143, the second inner conductive layer 147, the first outer conductive layer 145, and the second outer conductive layer 149 are formed for the first through holes 134 in the first solid electrolyte substrate 127 and the second through holes 133 in the second solid electrolyte substrate 125.

Thus, by executing the conductive-layer forming step subsequent to the insulator-layer forming step, it is possible to prevent the first conductive layer 137 and the second conductive layer 138 from coming into contact with the second solid electrolyte substrate 125 and the first solid electrolyte substrate 127, thereby making it possible to prevent short-circuiting.

In addition, in the method of manufacturing a sensor element in accordance with this embodiment, after forming the first outer conductive layer 145 on the first solid electrolyte substrate 127 and the second outer conductive layer 149 on the second solid electrolyte substrate 125 in the conductive-layer forming step, in the stacking step the second solid electrolyte substrate 125 and the first solid electrolyte substrate 127 are stacked while bringing the first outer conductive layer 145 and the second outer conductive layer 149 into contact with one another. Consequently, an excellent connection state is achieved between the first conductive layer 137 and the second conductive layer 138, which are respectively formed on the first solid electrolyte substrate 127 and the second solid electrolyte substrate 125.

In the above-described embodiment, the $NO_x$ sensor 2 corresponds to the gas sensor described in the summary of the invention; the gas sensor element 4 corresponds to the sensor element; the second solid electrolyte substrate 125 corresponds to the second solid electrolyte layer; the first solid electrolyte substrate 127 corresponds to the first solid electrolyte layer; the heating portion 131 of the heating resistor pattern 121 corresponds to the heating portion; and the inner intermediate insulating layer 129 corresponds to the intermediate insulating layer.

Further, the ceramic sleeve 6, the ceramic holder 51, and the talc rings 53 and 56 correspond to the supporting members of the gas sensor in accordance with the invention.

(4) Other Embodiments

The mode for carrying out the invention is not limited to the above-described embodiment, and it is possible to adopt various structures insofar as they fall within the technical scope of the invention.

For example, although in the above-described embodiment (hereafter, also referred to as the first embodiment) a description has been given of the gas sensor element 4 having an inner intermediate insulating layer 129 whose thicknesswise dimension is formed so as to be fixed from the leading end side to the rear end side of the solid electrolytes, the inner intermediate insulating layer which is disposed between the solid electrolytes is not limited to this form.

Accordingly, as a second embodiment, a description will be given of a second sensor element 204 having an inner intermediate insulating layer having a form in which the thicknesswise dimension in the heating-portion forming region and the thicknesswise dimension in a peripheral region of the outer conductive member differ.

Figure 7:
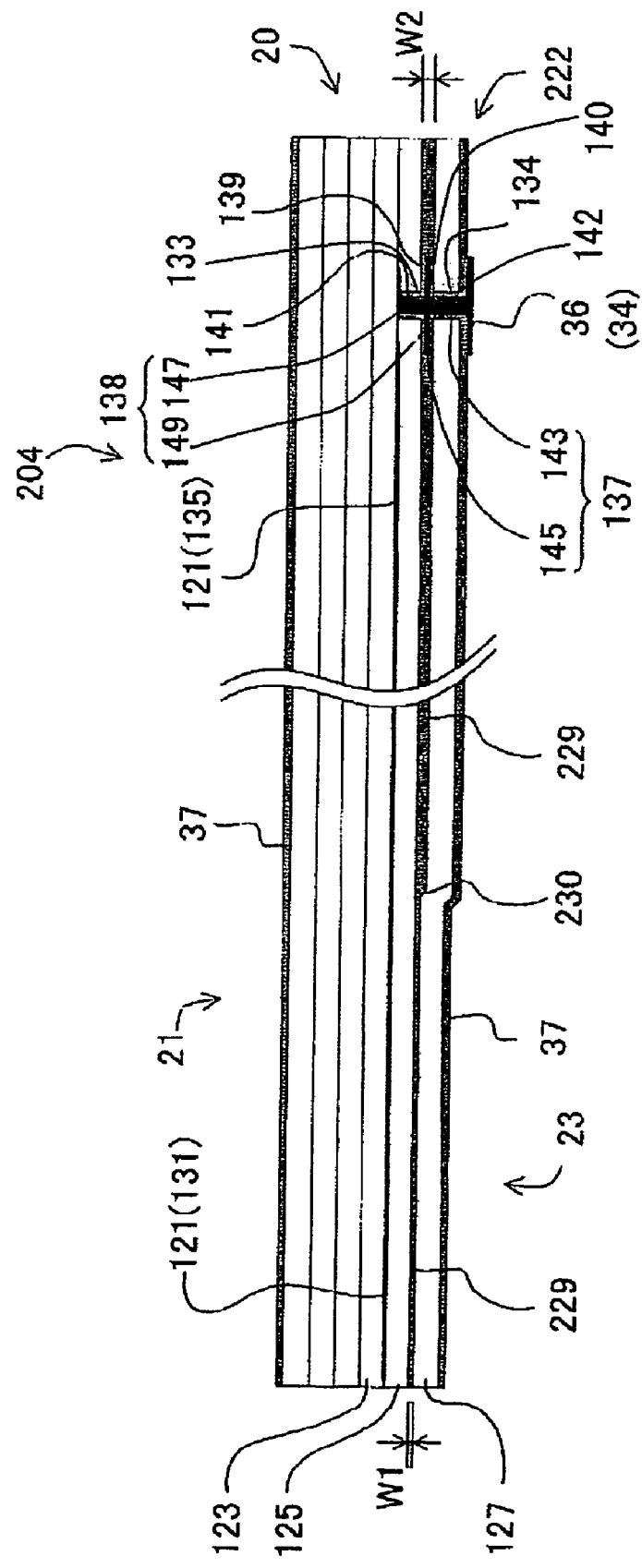
FIG. 7 is a cross-sectional view illustrating the internal structure of a second sensor element.

FIG. 7 shows a cross-sectional view illustrating the internal structure of the second sensor element 204. In FIG. 7, of the constituent elements of the second sensor element 204, constituent elements similar to those of the gas sensor element 4 of the first embodiment will be identified with the same reference numerals as those of the first embodiment.

The second sensor element 204 has the same shape of an elongated plate extending the axial direction as the gas sensor element 4, and is comprised of the detecting element 20, a second heater 222, the outer intermediate insulating layer 37, and the electrode terminal portions. Although the second sensor element 204 has the same electrode terminal portions 30, 31, 32, 33, 34 and 36 as the gas sensor element 4, only the electrode terminal portion 36 (34) is shown in FIG. 6, and illustration of the electrode terminal portions 30, 31, 32 and 33 is omitted.

The second heater 222 is comprised of the heating resistor pattern 121 composed principally of Pt; the three solid electrolyte substrates 123, 125 and 127 composed principally of zirconia; a second inner intermediate insulating layer 229 composed principally of alumina; the pair of electrode terminal portions 34 and 36 for connecting to an external circuit; and the two pairs of the first conductive layer 137 and the second conductive layer 138 composed principally of an electrically conductive material.

The heating resistor pattern 121 includes the heating portion 131 provided on the longitudinally leading end side (the left-hand side is the leading end side in FIG. 7) of the second heater 222, as well as the pair of heater lead portions 125 respectively extending toward the rear end side (the right-hand side is the leading end side in FIG. 7) from both end portions of the heating portion 131. The first conductive layer 137 and the second conductive layer 138 are provided to electrically connect the heating resistor pattern 121 and the electrode terminal portions 34 and 36. The first inner conductive layer 143 and the first outer conductive layer 145 constitute the first conductive layer, while the second inner conductive layer 147 and the second outer conductive layer 149 constitute in the second conductive layer.

The second heater 222 has the two pairs of the first through hole 134 and the second through hole 133 which are respectively formed on the longitudinally rear end side of the first solid electrolyte substrate 127 and the second solid electrolyte substrate 125.

The second inner intermediate insulating layer 229 is formed (between the second solid electrolyte substrate 125 and the first solid electrolyte substrate 127) not only on the rear end side where the first through holes 134 and the second through holes 133 are formed, but also on the leading end side where the heating portion 131 is formed.

The thicknesswise dimension W1 of the second inner intermediate insulating layer 229 on the leading end side where the heating portion 131 is formed is 20 μm, while the thicknesswise dimension W2 of the second inner intermediate insulating layer 229 on the rear end side where the first through holes 134 and the second through holes 133 are formed is 100 μm. In other words, the second inner intermediate insulating layer 229 has a form in which the thicknesswise dimension W1 on the leading end side is smaller than the thicknesswise dimension W2 on the rear end side.

In addition, the second inner intermediate insulating layer 229 of the second sensor element 204 has a dimension changing portion 230 formed between the second solid electrolyte substrate 125 and the first solid electrolyte substrate 127 such that the thicknesswise dimension of the second inner intermediate insulating layer 229 becomes smaller on the heating portion 131 side of the dimension changing portion 230.

Thus, in the second sensor element 204 having the heating portion 131, the leading end side where the heating portion 131 is provided assumes a higher temperature as compared with the rear end side where the first through holes 134 and the second through holes 133 are formed. Therefore, the exfoliation of the second solid electrolyte substrate 125 and the first solid electrolyte substrate 127 with respect to the inner intermediate insulating layer 129 due to a difference in thermal expansion tends to occur more frequently on the leading end side.

On the other hand, the second inner intermediate insulating layer 229 has a thicknesswise dimension W1 on the leading end side that is smaller than the thicknesswise dimension W2 on the rear end side. For this reason, a temperature difference between the respective portions in the thicknesswise direction is further suppressed on the leading end side (i.e., the portion where the heating portion 131 is formed) of the second sensor element 204 as compared with the rear end side thereof.

Hence, according to the second sensor element 204 of the second embodiment, even in cases where the heating portion 131 is provided, the arrangement is such that a temperature difference at the portion where the heating portion 131 is formed is suppressed, thereby making it possible to prevent breakage due to a difference in thermal expansion.

The leading end side of the second sensor element 204 is the side having a detecting portion which is exposed to the gas to be detected among opposing longitudinal ends of the second sensor element 204, and the rear end side of the second sensor element 204 is the side opposite the leading end side.

Furthermore, since the second inner intermediate insulating layer 229 has the dimension changing portion 230, the second inner intermediate insulating layer 229 assumes a form in which the thickness dimension W1 on the leading end side differs from the thickness dimension W2 on the rear end side.

Next, as still another embodiment, the inner intermediate insulating layer is not limited to one formed continuously from the rear end portion of the sensor element toward the leading end portion thereof, and may be formed at least on the rear end side where the through holes are formed.

Figure 8:
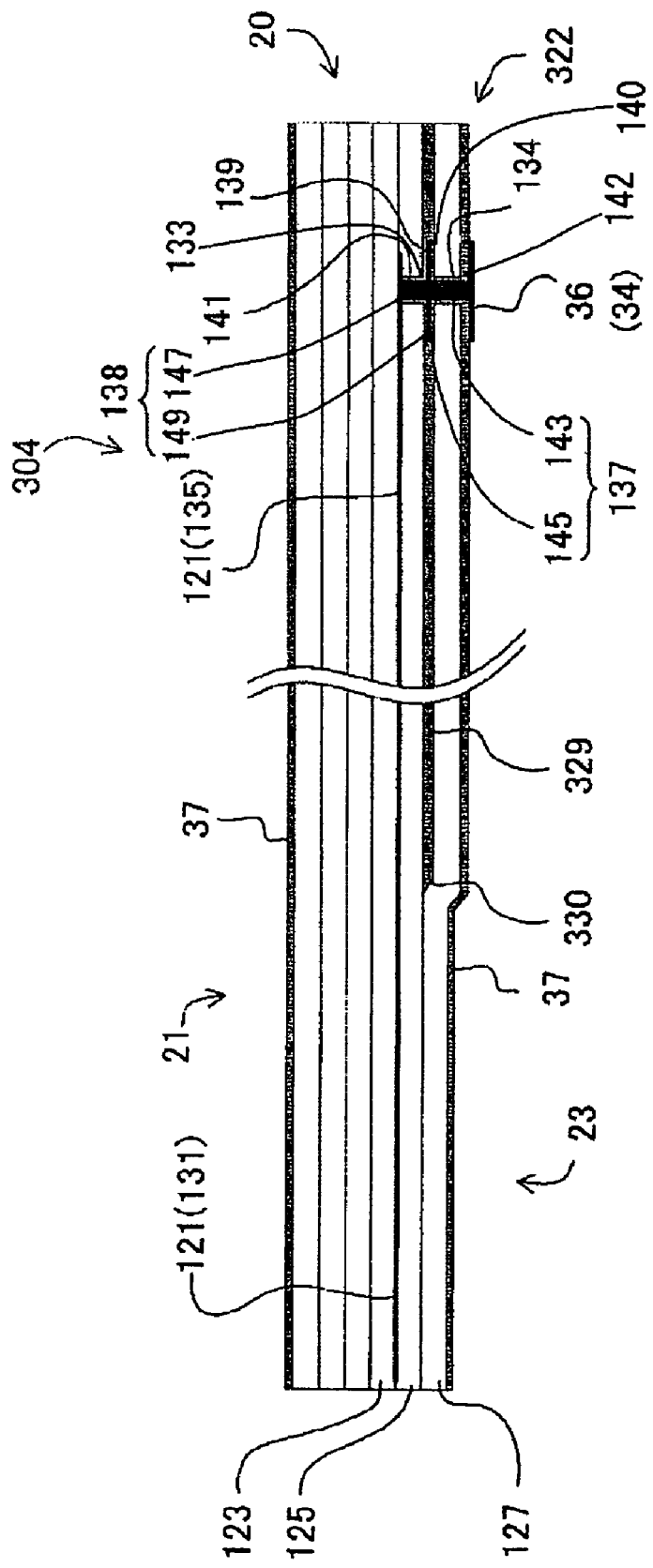
FIG. 8 is a cross-sectional view illustrating the internal structure of a third sensor element.

For example, in the case of a third inner intermediate insulating layer 329 which is provided in a third heater 322 of a third sensor element 304 shown in FIG. 8, the third inner intermediate insulating layer 329 is disposed at peripheral edges of the first through holes 134 and the second through holes 133, and not where the heating portion 131 is formed.

Figure 9:
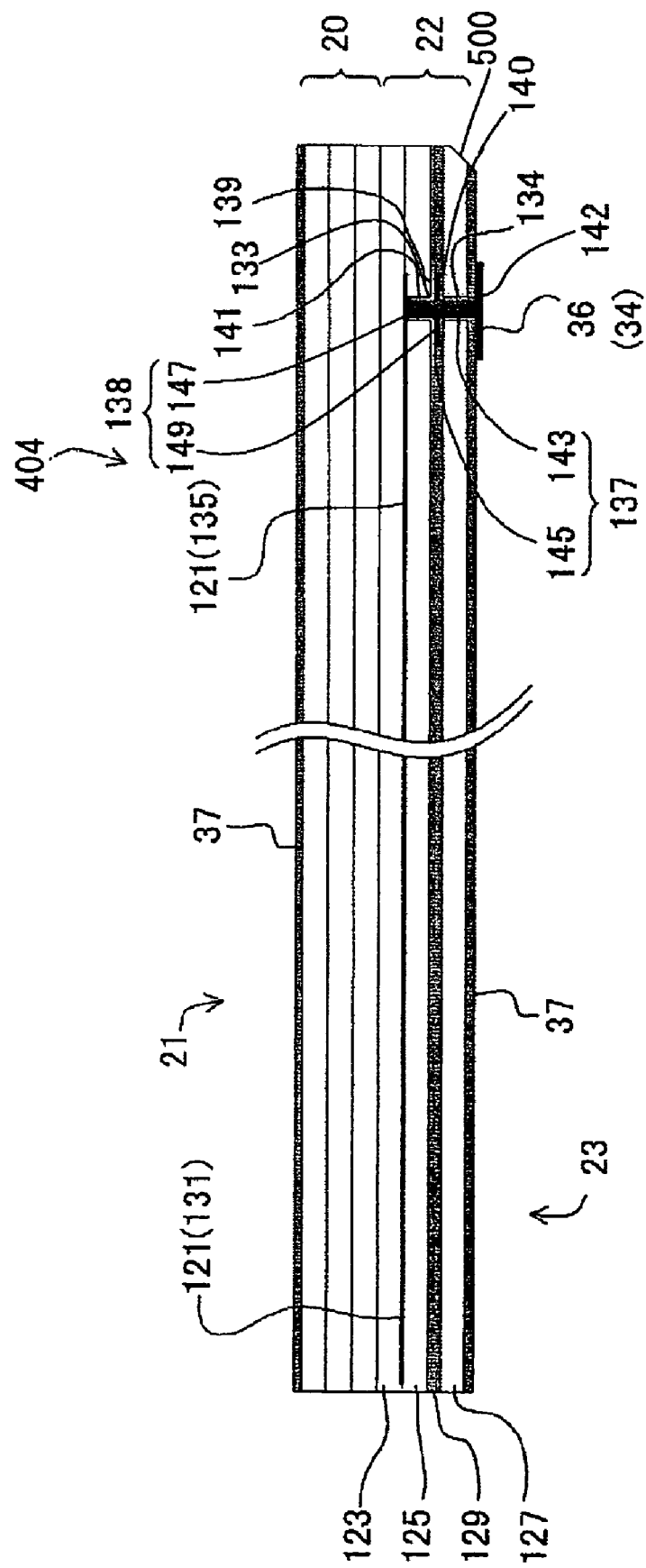
FIG. 9 is a cross-sectional view illustrating the internal structure of a fourth sensor element.

In addition, as a further embodiment, the form shown in FIG. 9 may be adopted. FIG. 9 is a cross-sectional view illustrating the internal structure of a fourth sensor element 404. In FIG. 9, of the constituent elements of the fourth sensor element 404, constituent elements similar to those of the gas sensor element 4 of the first embodiment will be identified by using the same reference numerals as those of the first embodiment.

As shown in FIG. 9, a chamfered portion 500 is formed on the rear end side of the sensor element 404. The chamfered portion 500 is provided to help protect the sensor element 404 from breaking. Further, the outer intermediate insulating layer 37 is exposed at the surface of the chamfered portion 500.

Since the outer intermediate insulating layer 37 is exposed at the chamfered portion 500, it is possible to reliably prevent the first solid electrolyte substrate 127 and the electrode terminal portions 34 and 36 from short-circuiting. The outer intermediate insulating layer 37 corresponds to the third outer insulating layer, and the electrode terminal portions 34 and 36 correspond to the third outer conductive layers.

In addition, although in the foregoing embodiments a description has been given of the sensor element having a heater, the invention may be applied to a sensor element that does not have a heater. In addition, the through holes and the conductive members which are applied in the invention are not limited to those which form energizing paths for connection to the heating resistor pattern, and may be those which form energizing paths for connection to the oxygen concentration detecting cell, the oxygen pump cell and the $NO_x$ cell.

It should further be apparent to those skilled in the art that various changes in form and detail of the invention as shown and described above may be made. It is intended that such changes be included within the spirit and scope of the claims appended hereto.

This application is based on Japanese Patent Application JP 2006-322248, filed Nov. 29, 2006, the entire content of which is hereby incorporated by reference, the same as if set forth at length.

What is claimed is:

1. A sensor element comprising:
    a first solid electrolyte layer having a first through hole which penetrates from a first obverse surface to a first reverse surface located on a side opposite the first obverse surface; and
    a second solid electrolyte layer having a second through hole which penetrates from a second obverse surface to a second reverse surface located on a side opposite the second obverse surface and which overlaps the first through hole in a penetrating direction, the second solid electrolyte layer being stacked on the first solid electrolyte layer by bringing the first reverse surface and the second obverse surface into contact with one another directly or through another member,
    the first solid electrolyte layer comprising a first inner insulating layer provided on an inner surface of the first through hole, a first outer insulating layer connected to the first inner insulating layer and provided on the first reverse surface, a first inner conductive layer provided on the first inner insulating layer, and a first outer conductive layer directly connected to the first inner conductive layer and provided on the first outer insulating layer,
    the second solid electrolyte layer comprising a second inner insulating layer provided on an inner surface of the second through hole, a second outer insulating layer connected to the second inner insulating layer and provided on the second obverse surface, a second inner conductive layer provided on the second inner insulating layer, and a second outer conductive layer directly connected to the second inner conductive layer and provided on the second outer insulating layer, and
    wherein the first outer conductive layer and the second outer conductive layer are in direct contact with one another and overlap one another in the penetrating direction.

2. The sensor element according to claim 1, wherein, when the first solid electrolyte layer is viewed in a direction perpendicular to a thicknesswise direction of the first solid electrolyte layer, the first outer insulating layer extends further from a periphery of the first through hole than the first outer conductive layer, and when the second solid electrolyte layer is viewed in a direction perpendicular to a thicknesswise direction of the second solid electrolyte layer, the second outer insulating layer extends further from a periphery of the second through hole than the second outer conductive layer.

3. The sensor element according to claim 2, wherein, when the first solid electrolyte layer is viewed in the direction perpendicular to the thicknesswise direction of the first solid electrolyte layer, the first outer insulating layer extends further than the first outer conductive layer by 0.1 mm or more, and when the second solid electrolyte layer is viewed in the direction perpendicular to the thicknesswise direction of the second solid electrolyte layer, the second outer insulating layer extends further than the second outer conductive layer by 0.1 mm or more.

4. The sensor element according to claim 2, wherein the first outer insulating layer and the second outer insulating layer are in contact with one another through an intermediate insulating layer.

5. The sensor element according to claim 4, wherein the first solid electrolyte layer and the second solid electrolyte layer are in contact with one another through the intermediate insulating layer.

6. The sensor element according to claim 5, wherein an interval dimension between the first reverse surface and the second obverse surface is in a range of from 10 μm to 100 μm.

7. The sensor element according to claim 4, wherein the first through hole and the second through hole are arranged in longitudinally rear end portions of the first solid electrolyte layer and the second solid electrolyte layer, respectively, and a heating portion is provided on a leading end portion of the sensor element,
    wherein the intermediate insulating layer is also provided on the leading end portion where the heating portion is located, between the first solid electrolyte layer and the second solid electrolyte layer, and
    a thicknesswise dimension of the intermediate insulating layer at the leading end side is smaller than a thicknesswise dimension of the intermediate insulating layer at the rear end portion where the first through hole and the second through hole are located.

8. The sensor element according to claim 7, wherein the intermediate insulating layer is provided continuously from the leading end portion to the rear end portion of the sensor element between the first solid electrolyte layer and the second solid electrolyte layer, and has a dimension changing portion at which the thicknesswise dimension of the intermediate insulating layer changes so as to become smaller on a leading end portion side of the dimension changing portion.

9. The sensor element according to claim 1, further comprising:
   a third outer insulating layer provided on the first obverse surface and connected to the first inner insulating layer and a third outer conductive layer which is provided on the third outer insulating layer and which is connected to the first inner conductive layer, and
   a chamfered portion provided on a longitudinally rear end side of the first solid electrolyte layer, the third outer insulating layer being exposed at a surface of the chamfered portion.

10. A method for manufacturing a sensor element, said sensor element comprising a first solid electrolyte layer having a first through hole which penetrates from a first obverse surface to a first reverse surface located on a side opposite the first obverse surface and a second solid electrolyte layer having a second through hole which penetrates from a second obverse surface to a second reverse surface located on a side opposite the second obverse surface and which connects to overlaps the first through hole in a penetrating direction, the second solid electrolyte layer being stacked on the first solid electrolyte layer by bringing the first reverse surface and the second obverse surface into contact with one another directly or through another member, the first solid electrolyte layer comprising a first inner insulating layer provided on an inner surface of the first through hole, a first outer insulating layer connected to the first inner insulating layer and provided on the first reverse surface, a first inner conductive layer provided on the first inner insulating layer, and a first outer conductive layer directly connected to the first inner conductive layer and provided on the first outer insulating layer, the second solid electrolyte layer comprising a second inner insulating layer provided on an inner surface of the second through hole, a second outer insulating layer connected to the second inner insulating layer and provided on the second obverse surface, a second inner conductive layer provided on the second inner insulating layer, and a second outer conductive layer directly connected to the second inner conductive layer and provided on the second outer insulating layer, and wherein the first outer conductive layer and the second outer conductive layer are in direct contact with one another and overlap one another in the penetrating direction, the method comprising:
   forming an insulating layer which comprises forming said first inner insulating layer on an inner surface of the first through hole of the first solid electrolyte layer before stacking, forming on the first reverse surface said first outer insulating layer which is connected to the first inner insulating layer, forming said second inner insulating layer on an inner surface of the second through hole of the second solid electrolyte layer, and forming said second outer insulating layer which is connected to the second inner insulating layer on the second obverse surface;
   forming said conductive layer which comprises forming said first inner conductive layer on the first inner insulating layer, forming on the first outer insulating layer said first outer conductive layer which is connected to the first inner conductive layer forming said second inner conductive layer on the second inner insulating layer, and forming on the second outer insulating layer said second outer conductive layer which is connected to the second inner conductive layer; and
   stacking the first solid electrolyte layer and the second solid electrolyte layer while the first outer conductive layer and the second outer conductive layer are brought into direct contact with one another.

11. The sensor element according to claim 1, wherein the second outer conductive layer is directly connected to the second inner conductive layer.

* * * * *